(12) United States Patent
Lenfers et al.

(10) Patent No.: US 6,270,639 B1
(45) Date of Patent: Aug. 7, 2001

(54) ELECTROCHEMICAL SENSOR

(75) Inventors: Martin Lenfers, Aidlingen; Olaf Jach, Boeblingen; Harald Neumann, Vaihingen; Walter Strassner, Schorndorf; Johann Riegel, Bietigheim-Bissingen; Lothar Diehl, Stuttgart, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/239,291

(22) Filed: Jan. 29, 1999

(30) Foreign Application Priority Data

Jan. 30, 1998 (DE) .............................. 198 03 532

(51) Int. Cl.[7] .................... G01N 27/409; G01N 27/41
(52) U.S. Cl. .................. 204/425; 204/426; 204/427
(58) Field of Search .................. 204/426, 425, 204/424, 427, 428, 429; 205/783.5, 784, 784.5, 785

(56) References Cited

U.S. PATENT DOCUMENTS

| | | | |
|---|---|---|---|
| 4,505,807 | * | 3/1985 | Yamada ............................. 204/425 |
| 4,755,274 | * | 7/1988 | Mase et al. ....................... 204/427 |
| 4,798,693 | * | 1/1989 | Mase et al. ....................... 264/44 |
| 4,897,174 | * | 1/1990 | Wang et al. ...................... 204/425 |
| 4,981,125 | * | 1/1991 | Kato et al. ....................... 204/406 |
| 5,098,549 | * | 3/1992 | Friese et al. ...................... 204/425 |
| 5,169,512 | | 12/1992 | Wiedenmann et al. . |
| 5,236,569 | * | 8/1993 | Murase et al. ..................... 204/412 |
| 5,298,147 | * | 3/1994 | Nakae et al. ...................... 204/424 |

FOREIGN PATENT DOCUMENTS 38 11 713    10/1989  (DE) .

* cited by examiner

Primary Examiner—Robert J. Warden, Sr.
Assistant Examiner—Kaj K. Olsen
(74) Attorney, Agent, or Firm—Kenyon & Kenyon

(57) ABSTRACT

An electrochemical sensor determining a gas concentration of the measuring gas. The sensor has an electrochemical element including a first solid electrolyte body having an electrochemical pump cell and a first (external pump) and a second (internal pump) electrode and having a gas chamber which is connected to the measuring gas chamber via a gas supply opening and in which the second electrode is arranged. The electrochemical element also includes a second solid electrolyte body having an electrochemical sensor cell (e.g., a Nernst cell) and a third and fourth electrode, each electrode having a lead for the electrical contacting. The leads of the first and second electrodes are decoupled capacitively from the lead of at least the fourth electrode by a device.

6 Claims, 2 Drawing Sheets

ELECTROCHEMICAL SENSOR

BACKGROUND INFORMATION

Conventional electrochemical sensors generally include an electrochemical element, which has an electrochemical pump cell having a preferably planar, first solid electrolyte body and a first and second preferably porous electrode. These conventional sensors also include an electrochemical sensor cell having a preferably planar, second solid electrolyte body and a third and fourth preferably porous electrode. The sensor has a gas supply opening which includes a gas supply channel which, on the one hand, is connected to a measuring gas chamber, and on the other hand, is connected to a hollow space surrounded by the two solid electrolyte bodies.

A diffusion resistance device, which can contain a porous filling, is arranged in the measuring gas chamber.

The measuring gas arrives in the measuring gas chamber via the gas supply opening and the gas supply channel, the first and the second electrodes of the pump cell acting to regulate the admission of the measuring gas into the gas chamber and thus assure a controlled partial pressure of the gas components to be measured. The electrochemical difference in potential between the electrodes of the second solid electrolyte body arises due to the varying gas partial pressures in the diffusion resistance device and in a reference gas chamber, arranged, for example, in the second solid electrolyte body. The difference in potential can be measured by a voltmeter situated outside the electrochemical element.

The conventional sensors described above, referred to as planar wideband-lambda probes, have been used, for example, in the technology of catalytic exhaust emission control systems for internal combustion engines. A typical design of one such conventional electrochemical sensor is described in German Patent Application No. 38 11 713. The conventional sensors have a disadvantage that they have a so-called lambda=1 ripple, particularly in high operating temperatures. This leads to problems in control processes in which the lambda value represents the control variable. As a result of the ripple of the lambda signal, it is in many cases impossible to make an adjustment for an output quantity value to be sufficiently stable.

SUMMARY OF THE INVENTION

The present invention provides an electrochemical sensor for determining the concentration of a gas (e.g., a concentration of oxygen) in a measuring gas, and having an electrochemical element. The sensor includes a first solid electrolyte body having an electrochemical pump cell and a first (external pump) and a second (internal pump) electrode. In addition, the sensor has a gas chamber, which is connected via the gas supply opening and a gas supply channel to the measuring gas chamber, and in which one of the two electrodes is arranged. Furthermore, a second solid electrolyte body is provides which has an electrochemical sensor cell (e.g., Nernst cell), which includes a third and fourth electrode. Each electrode has a lead for the purpose of electrical contacting.

According to the present invention, leads of the first and second electrodes are capacitively decoupled from the lead of at least the fourth electrode with the assistance of a device. Thus, capacitive couplings of the electrode leads in conventional electrochemical sensors can lead to a reaction of the pump voltage on the Nernst voltage of the sensor cell and that this, in turn, particularly at high temperatures, is one cause for the undesirable phenomenon of the lambda=1 ripple (i.e., undershooting or overshooting of the output signal in response to violent fluctuations in the gas exchange).

As a result of the capacitive decoupling of the electrode leads according to the present invention, the lamdba=1 ripple is advantageously reduced or even prevented.

In an exemplary embodiment of the present invention, a device causing the decoupling is formed by the lead of the second electrode. In particular, the leads of the first and second electrodes are arranged with a clearance to be situated one on top of the other. In this manner, a coupling of the pump voltage into the sensor cell is avoided, so that the lamdba=1 ripple is at least reduced.

In another embodiment of the present invention, the leads of the first and second electrodes are arranged in the center in the electrochemical element. In this manner, the one-over-the-other positioning of the two electrode leads (as described above) is attained in a simple manner.

An exemplary embodiment of the present invention provides that the leads of all electrodes are arranged with a clearance to be one on top of the other. In this manner, a coupling of a voltage into the sensor cell is avoided. In particular, this holds true for a sensor heating element. This means that the leads for the heating element can also be situated below or above the leads of the electrodes.

In another exemplary embodiment of the present invention, the device for the capacitive decoupling is formed through an electron-conductive layer, which can also be a foil binder layer. This foil binder layer preferably joins the first and second electrolyte bodies to each other and is therefore a part of the solid electrolyte body that is performing the coupling.

Another exemplary embodiment of the present invention provides that the layer is connected in an electrically conductive manner to the second electrode. Alternatively, it is also possible that the layer has its own lead extending out from the electrochemical element as a contact.

In another exemplary embodiment of the present invention, the foil binder layer has a doping using cerium dioxide or titanium dioxide.

Electrochemical sensors according to the present invention and their electrochemical elements are advantageously manufactured starting with plateshaped or foil-shaped oxygen-conducting solid electrolytes, for example, made of stabilized zirconium dioxide, and coating them on both sides with an interior and exterior pump electrode, respectively, having the appropriate printed circuit traces. In this manner, the inner pump electrode is located advantageously in the edge area of a diffusion or gas supply channel, through which the measuring gas is delivered, and which functions as the gas diffusion resistance. The pump cell obtained in this manner can then be laminated together with a sensor cell (e.g., the Nernst cell) that is manufactured in a similar way and is composed of a second, formed solid electrolyte foil, and can be sintered, for example, at 1300 to 1550° C.

For manufacturing porous fillers, the process starts, for example, with providing porously sintering foil inserts made of a ceramic material and which has suitable thermal properties of expansion that closely correspond to those of the solid electrolyte foils used. It is advantageous if, for the filling, a foil insert is used made of the ceramic material which the solid electrolyte foils are also made of, it being possible to induce the porosity of the insert using pore-forming materials such as thermal carbon powder, organic plastics, or salts, which, during the sintering process, burn, decompose, or evaporate. The output materials are used in concentration such that, after the sintering, porosities of 10 to 50%, preferably 40%, are achieved, the average pore diameter being approximately 5 to 50 μm, preferably 10 μm.

The present invention also relates to wideband-lambda probes for determining the lambda value of gas mixtures in internal combustion engines. The lambda value or the "air number", in this context, is defined as the relationship of the prevailing air-fuel ratio to the stoichiometric air-fuel ratio. The probes measure the oxygen content of the exhaust gas above a change in the limiting current.

DETAILED DESCRIPTION

Figure 1:
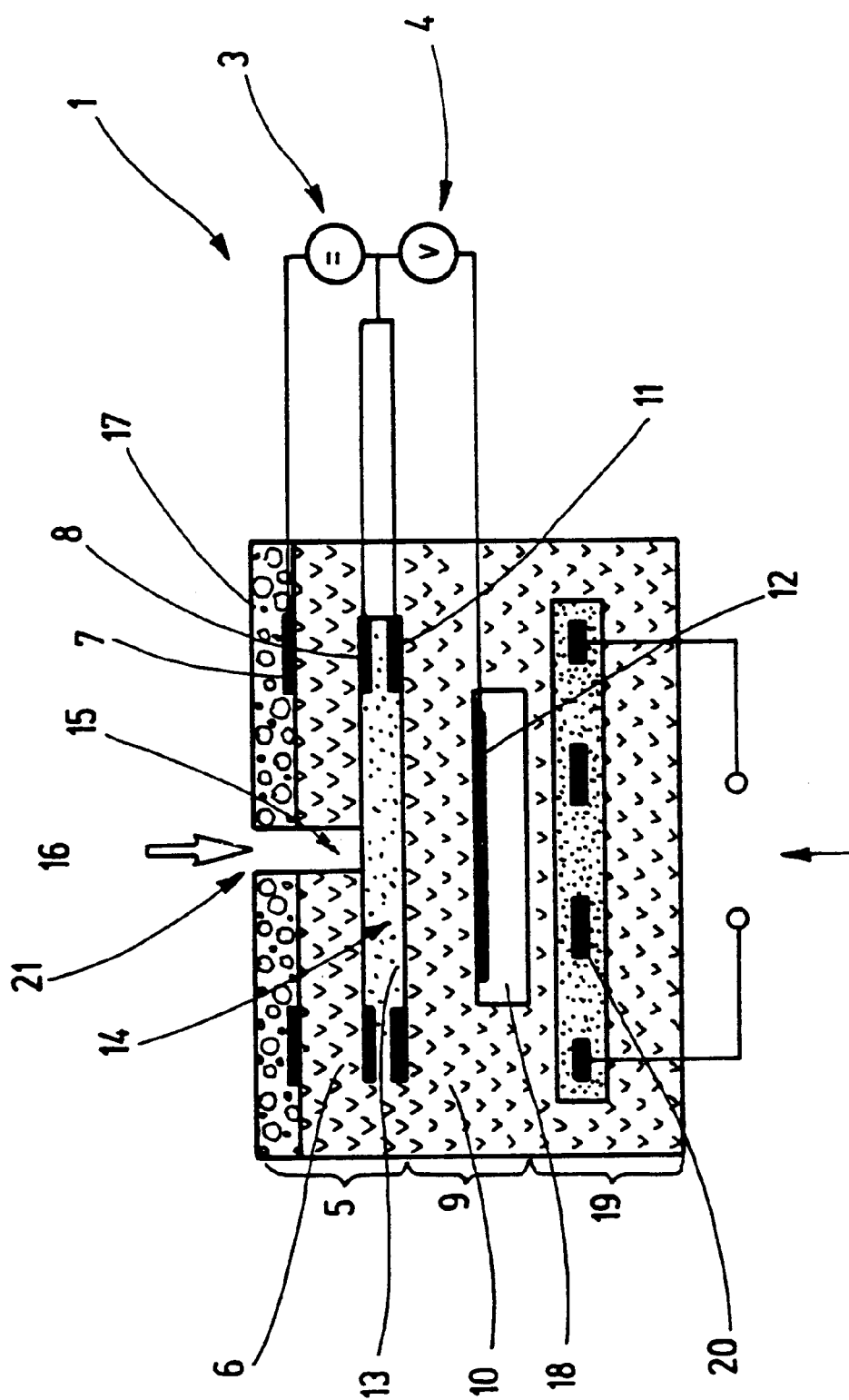
FIG. 1 shows an electrochemical sensor.

FIG. 1 shows a cross sectional view of an electrochemical sensor 1, which has an electrochemical element 2, and a voltage supply device 3. In addition, FIG. 1 also shows an evaluating device which measures the output voltage or the output current of electrochemical element 2.

Electrochemical element 2 has an electrochemical pump cell 5, which is composed of a first planar solid electrolyte body 6, a first porous electrode 7, and a second porous electrode 8. Electrochemical element 2 also has an electrochemical sensor cell (Nernst cell) 9, which is composed of a second solid electrolyte body 10, as well as a third electrode 11 and a fourth electrode 12. Pump cell 5 is supplied with voltage at first and second electrode 7, 8, with the assistance of external voltage supply device 3. First and second solid electrolyte bodies 6, 10 are joined to each other and surround an inner hollow space 14 which is also designated as gas chamber 13. Inner hollow space 14 is completely filled with a porous material and contains second and third electrodes 8, 11. Gas chamber 13 is connected to a measuring gas chamber 16 via a gas supply channel 15 which is partially loaded with a porous filling. The surface of first solid electrolyte body 6, facing measuring gas chamber 16, is covered by a porous ceramic protective layer 17. Second solid electrolyte body 10 has a reference gas chamber 18. A fourth electrode 12 is arranged in the reference gas chamber 18, and is exposed to a reference gas to constitute a reference electrode.

Electrochemical element 2 also includes a third solid electrolyte body 19, which contains a heating device 20 and is joined to second solid electrolyte body 10.

The measuring gas arrives in gas chamber 13 via gas supply opening 21 and gas supply channel 15, a controlled partial pressure being adjusted by a pump voltage applied at first and second electrodes 7, 8 of pump cell 5, through pumping oxygen in or out.

Because of the varying gas partial pressures in gas chamber 13 and in reference gas chamber 18, which is disposed in second solid electrolyte body 10, an electrochemical difference in potential arises between third and fourth electrodes 11, 12 of second electrolyte body 10, the difference being measured by a voltmeter 4 (e.g., an evaluating device) situated outside the electrochemical element.

Figure 2:
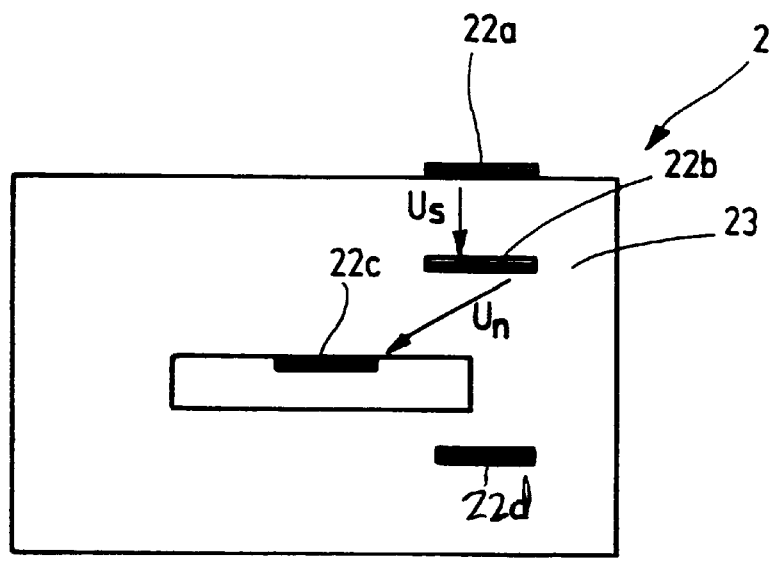
FIG. 2 shows a first exemplary embodiment of a device for the capacitive decoupling of electrode leads according to the present invention.

FIG. 2 shows a simplified, cross-sectional representation of electrochemical sensor 2 illustrated in FIG. 1 in the area of the leads, formed as printed circuit traces, of electrodes 7, 8, 11, and 12, as well as of heating element 20. The sectional plane of electrochemical sensor 2 shown in FIG. 2 is parallel to the plane of the drawing and of the plane of FIG. 1. A lead 22a forms the lead for first electrode 7; a lead 22b enables a contacting of electrodes 8 and 11; a lead 22c is assigned to fourth electrode 12, and a lead 22d contacts heating element 20.

Between leads 22a and 22b is pump voltage $U_s$, which is also available at eletrodes 7, 8. Leads 22b and 22c carrying the so-called Nernst voltage (sensor voltage) $U_n$, which is applied at electrodes 11, 12. FIG. 2 shows that pump voltage $U_s$ is not coupled into Nernst voltage $U_n$. Lead 22b of electrodes 7, 11 functions as device 23 for the capacitive decoupling of pump voltage $U_s$ from Nernst voltage $U_n$. Leads 22a and 22b are arranged with a clearance, one on top of the other. Lead 22b, viewed in a top view of FIG. 2, is essentially covered by lead 22a. Using a device 23, the two volt age s are decoupled so that during operation, particularly at high temperatures, Nernst voltage $U_n$, also designated as output voltage, does not exert any influence. Therefore, a slight lamdba=1 ripple arises in electrochemical element 2.

Figure 3:
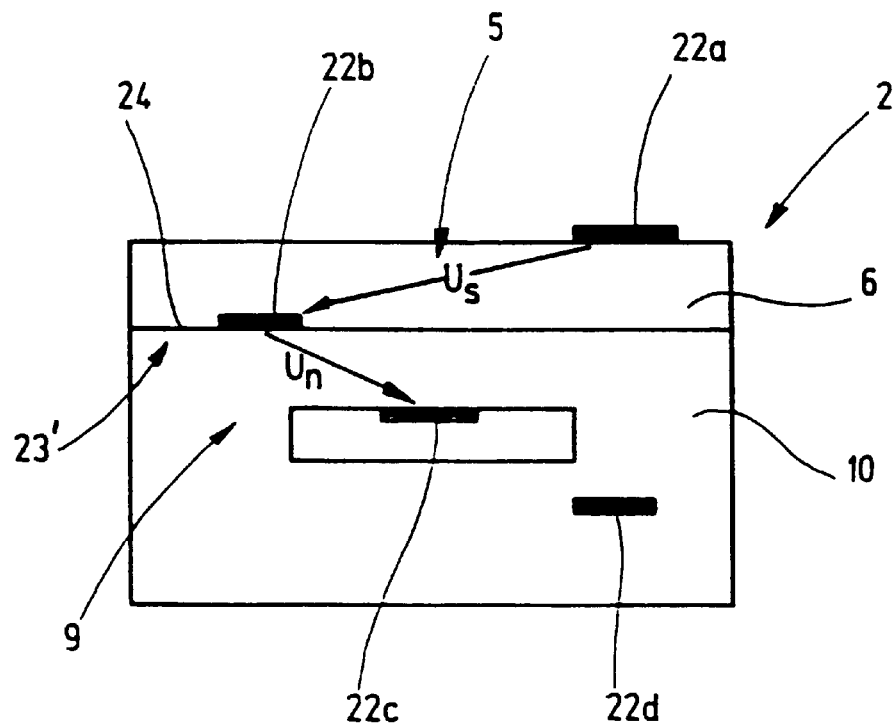
FIG. 3 shows a second exemplary embodiment of the device for the capacitive decoupling of the electrode lead according to the present invention.

FIG. 3 shows a simplified, cross-sectional representation of a second exemplary embodiment of electrochemical element 2. The same parts having the same reference numerals as shown in FIG. 2 are also used in FIG. 3. In contrast to the exemplary embodiment shown in FIG. 2, electrodes 22a and 22b are not situated directly one on top of the other. Therefore, within first solid electrolyte body 6 arises pump voltage $U_s$ according to the drawn-in voltage-arrow. Nernst voltage $U_n$ is available between leads 22b and 22c. In order to prevent pump voltage $U_s$ from being coupled into Nernst voltage $U_n$, a device 23' is provided which is formed by a layer 24. This layer 24 is an electrically conductive foil binder layer, which can join first solid electrolyte body 6 and second solid electrolyte body 10 to each other. The foil binderm layer can be doped with one of cerium dioxide and titanium dioxide. As a result of the electrical conductivity of layer 24, a capacitive decoupling between pump cell 5 and sensor cell 9 is achieved, since layer 24 is connected to lead 22b in an electrically conductive manner to provide a screening device. It is also possible to contact layer 24 separately, maintaining it, however, at the same electrical potential as lead 22b. Layer 24 extends between leads 22b and 22c, without covering the associated, preferably ring-shaped electrodes. The sensor can also have the respective leads of the first, second, third, and fourth electrodes disposed on top of one another at a predetermined distance from one another.

What is claimed is:

1. An electrochemical sensor for determining a gas concentration of a measuring gas, said sensor having a layered design, comprising:

an electrochemical pump cell having a first electrolyte body, a first electrode and a second electrode, the first electrode being disposed on the first electrolyte body, the first electrolyte body including a pump gas chamber which is connected via a gas supply opening to a measuring gas chamber, the second electrode being disposed in the pump gas chamber; and an electrochemical sensor cell having a second electrolyte body, a third electrode and a fourth electrode, the third electrode being disposed in the pump gas chamber;

wherein a first lead electrically contacts the first electrode, a second lead electrically contacts the second and the third electrodes, and the fourth electrode has a third lead for an electrical contact, wherein the second lead lies in a plane of stratification between the first lead and the third lead, and wherein the first lead is capacitively decoupled from the third lead by an electron-conducting layer, the electron-conducting layer being disposed in a plane of stratification between the first lead and the third lead, and wherein the width of the electron-conducting layer substantially corresponds to the width of the electrochemical sensor.

2. The electrochemical sensor according to claim 1, wherein the electron-conducting layer is disposed between the first electrolyte body and the second electrolyte body.

3. The electrochemical sensor according to claim 1, wherein the electron-conducting layer is electrically connected to the second lead.

4. The electrochemical sensor according to claim 1, wherein the electron-conducting layer is a foil binder layer.

5. The sensor according to claim 4, wherein the foil binder layer is doped with one of cerium dioxide and titanium dioxide.

6. An electrochemical sensor for determining a gas concentration of a measuring gas, said sensor having a layered design, comprising:

an electrochemical pump cell having a first electrolyte body, a first electrode and a second electrode, the first electrode being disposed on the first electrolyte body, the first electrolyte body including a pump gas chamber which is connected via a gas supply opening to a measuring gas chamber, the second electrode being disposed in the pump gas chamber; and an electrochemical sensor cell having a second electrolyte body, a third electrode and a fourth electrode, the third electrode being disposed in the pump gas chamber;

wherein the first electrode has a first lead for an electrical contact, the second electrode has a second lead for an electrical contact, the third electrode has a third lead for an electrical contact, and the fourth electrode has a fourth lead for an electrical contact, and wherein the first lead is capacitively decoupled from the fourth lead by an electron-conducting layer, the electron-conducting layer being disposed in a plane of stratification between the first lead and the fourth lead, and wherein the width of the electron-conducting layer substantially corresponds to the width of the electrochemical sensor.

* * * * *